United States Patent [19]

Dean

[11] Patent Number: 4,532,301

[45] Date of Patent: Jul. 30, 1985

[54] RADIAL BLOCK POLYMERS

[75] Inventor: Barry D. Dean, Broomall, Pa.

[73] Assignee: Atlantic Richfield Company, Los Angeles, Calif.

[21] Appl. No.: 668,060

[22] Filed: Nov. 5, 1984

[51] Int. Cl.$^3$ .................................... C08F 293/00
[52] U.S. Cl. .................................... 525/280; 525/285; 525/308
[58] Field of Search ............... 526/204; 525/375, 280, 525/308, 285, 294

[56] References Cited

U.S. PATENT DOCUMENTS 4,075,286  2/1978  MacLeay ............... 525/308

Primary Examiner—Paul R. Michl
Attorney, Agent, or Firm—Dennis M. Kozak

[57] ABSTRACT

Radial block polymers having at least four arms. In one embodiment, the radial block polymers are prepared using a bisdiazobicyclooctane polymerization initiator. In another embodiment, five arm radial block polymers of this invention are well suited for use as impact modifiers for thermoformable plastic resins.

10 Claims, No Drawings

RADIAL BLOCK POLYMERS

This invention relates to radial block polymers.

More specifically, this invention relates to radial block polymers having at least four arms.

In one of its more specific aspects, this invention pertains to the utilization of a bisdiazobicyclooctane polymerization initiator having two azo linkages which initiate the free radical polymerization of a free radical polymerizable monomer. The initiator also has a α-carboxy carbonylazide moiety which can undergo a condensation reaction with one hydroxyl, amine or mercapto terminated polymer, to form the fifth arm of a radial block polymer.

In one embodiment, radial block polymers of this invention serve as excellent impact modifiers when incorporated into thermoformable plastic resins.

According to this invention, there is provided a radial block polymer having at least four arms and having the following general formula:

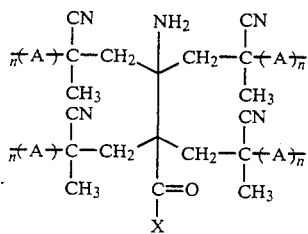

wherein each R separately represents a methyl or ethyl moiety; each A separately represents at least one free radically polymerizable monomer; X represents —OH, O(B)n, S(B)$_n$ or NH(B)$_n$; B represents at least one free radically polymerizable monomer; and, each n separately represents an integer greater than or equal to 50.

Also, according to this invention there is provided a moldable composition comprising a thermoformable plastic resin and a radial block polymer having the following general formula:

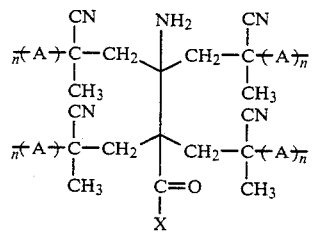

wherein each R separately represents a methyl or ethyl moiety; each A separately represents at least one free radically polymerizable monomer; X represents —OH, O—(B)$_n$, S(B)$_n$, NH(B)$_n$; B represents at least one free radically polymerizable monomer; and, each n separately represents an integer greater than or equal to 50.

Also, according to this invention there is provided a method of producing a molded composition which comprises forming a blend comprising a thermoformable plastic resin and a radial block polymer having the following general formula:

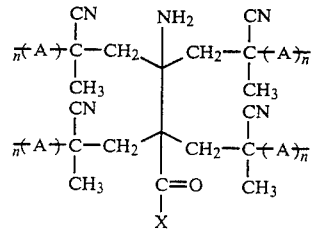

wherein each R separately represents a methyl or ethyl moiety; each A separately represents at least one free radically polymerizable monomer; X represents —OH, —O(B)$_n$, —S(B)$_n$, or NH(B)$_n$; B represents at least one free radically polymerizable monomer and, each n separately represents an integer greater than or equal to 50, and molding the resulting blend.

According to this invention there is also provided a molded composition comprising a continuous phase comprising a thermoformable plastic resin and a disperse phase within the continuous phase, the disperse phase being a radial block polymer having the following general formula:

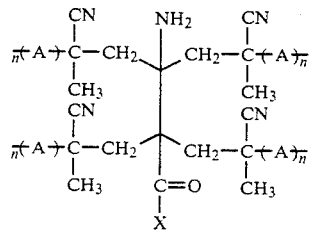

wherein each R separately represents a methyl or ethyl moiety; each A separately represents at least one free radically polymerizable monomer; X represents —OH, —O(B)$_n$, —S(B)$_n$, —NH(B)$_n$; B represents at least one free radically polymerizable monomer; and, each n separately represents an integer greater than or equal to 50.

Also, according to this invention there is provided a method of improving the impact resistance of a thermoformable plastic resin upon molding which comprises incorporating into a continuous phase thermoformable plastic resin, a disperse phase comprising a five-arm radial block polymer having the following general formula:

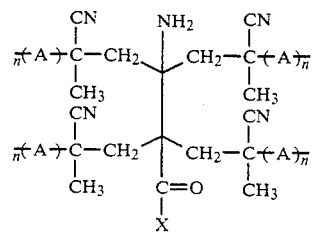

wherein each R separately represents a methyl or ethyl moiety; each A separately represents at least one free radically polymerizable monomer having a glass transition temperature $\leq 0°$ C.; X represents —O(B)$_n$, —S(B)$_n$ or —NH(B)$_n$; B represents at least one free radically polymerizable monomer having a glass transition temperature $\geq 25°$ C.; and, each n separately represents an integer greater than or equal to 50, the radial block polymer being incorporated in an amount sufficient to improve the impact resistance of the thermoformable plastic resin upon molding.

In the preceeding statements of invention, the upper limit for n is limited only by the reaction conditions under which the polymerization is carried out.

As the initiator to produce the radial block polymers of this invention use is made of [2,5,8,11]-tetraalkyl-[2,5,8,11]-tetracyano-cis 6a' carboxy, 12a' oxoazide-3,4:9,10 bisdiazobicyclooctane compounds having the general formula:

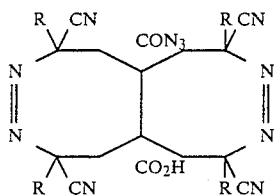

wherein each R separately represents a methyl or ethyl moiety.

Inasmuch as the above initiators are not commercially available, the following reaction sequence and Examples I–IV demonstrate their preparation.

The initiator is prepared according to the following reaction sequence in which each R separately represents a methyl or ethyl moiety:

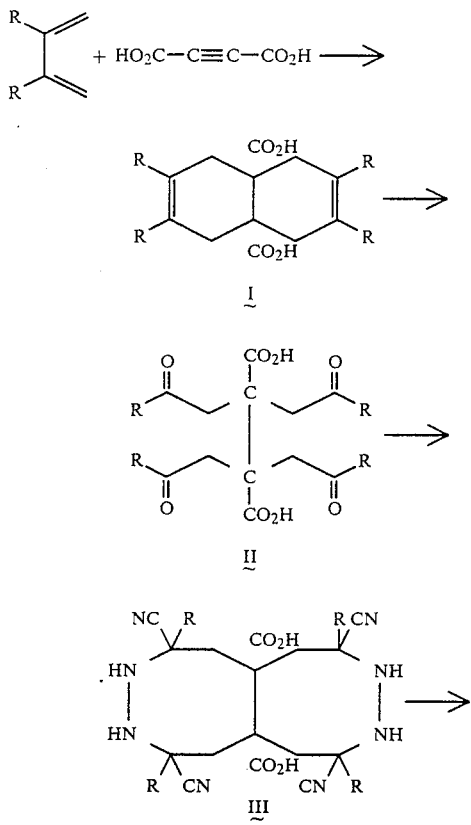

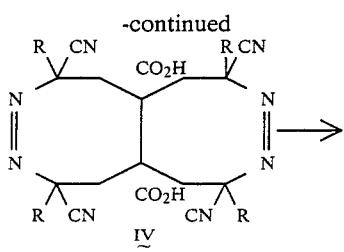

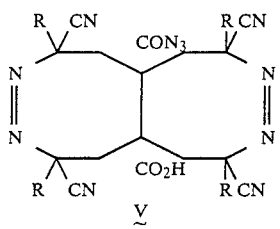

In the practice of this invention, the two azo linkages on the initiator are thermally activated to form radical species which will initiate the free radical polymerization or four polymer molecules.

Any free radically polymerizable monomer(s) can be employed to produce the $(A)_n$ and $(B)_n$ arms on the radial block polymers of this invention.

Suitable monomers include the acrylates; conjugated dienes; the styrenics; $\alpha, \beta$-unsaturated nitriles; $\alpha, \beta$-unsaturated acids and their esters; $\alpha, \beta$-unsaturated dicarboxylic acid anhydrides and their imide derivatives and the like, and their mixtures.

Partcularly suitable monomers include: ethylacrylate, n-butylacrylate, isobutylacrylate, 2-ethylhexylacrylate, isobornylacrylate, tertiary butylacrylate, secondary butylacrylate, n-propylacrylate, isopropylacrylate, 1,3-butadiene, isoprene, methylacrylate styrene, methacrylic acid, methylmethacrylate, maleic anhydride, N-phenylmaleimide, acrylonitrile, citraconic anhydride, dibromostyrene, t-butylstyrene, $\alpha$-methylstyrene, p-methylstyrene and the like and their mixtures.

If the radial block polymer of this invention is to be utilized to impact modify thermoformable plastic resins, it has been found preferable to formulate the radial block polymer to have five arms such that each $(A)_n$ arm is comprised of recurring units of one or more free radically polymerizable monomers having glass transition temperatures of less than or equal to 0° C. and the $(B)_n$ arm is comprised of recurring units of one or more free radically polymerizable monomers having glass transition temperatures of greater than or equal to 25° C.

Suitable free radically polymerizable monomers having Tg's $\leq 0°$ C. include ethylacrylate, n-butylacrylate, isobutylacrylate, 2-ethylhexylacrylate, isobornylacrylate, tertiary butylacrylate, secondary butylacrylate, n-propylacrylate, isopropylacrylate, 1,3-butadiene, isoprene and the like, and their mixtures.

Suitable free radically polymerizable monomers having Tg's $\geq 25°$ C. include styrene, methacrylic acid, methylmethacrylate, maleic anhydride, N-phenylmaleimide, acrylonitrile, citraconic anhydride, dibromostyrene, t-butylstyrene, $\alpha$-methylstyrene, p-methylstyrene and the like and their mixtures.

To produce a five arm radial block polymer of this invention the $\gamma$-carboxy carbonylazide moiety on the initiator is reacted with a polymer which has first been hydroxy, amine, or mercapto terminated using any conventional method, for example, the methods of Examples 5 and 6.

The following examples demonstrate the preparation of firstly, the bisdiazobicyclooctane initiator utilized in this invention (Examples 1–4) secondly, the preparation of three radical block polymers of this invention (Examples 5–7) and, lastly, four molding compositions of this invention (Examples 8–11).

The molding compositions of Examples 8–11 were molded into test specimens using a Battenfeld injection molding machine and the evaluation of material properties for the molded compositions was performed based on the following ASTM standard tests: flexural strength and modulus (D-790), tensile strength (D-638), notched Izod (D-256), and DTUL (deflection temperature under load at 256 psi) D-248. Gardner falling weight index ("GFWI") was established using a 1¼" diameter orifice and an 8 pound ½" diameter weight.

EXAMPLE 1

This example demonstrates the preparation of the above compound represented by Structure I.

Acetylene dicarboxylic acid (22.8 grams, 0.20 mole) and 2,3-dimethyl-1,3-butadiene (32.9 grams, 0.40 mole) were dissolved in 75 milliliters of a (60:40) chlorobenzene/dimethylformamide solution.

Zinc chloride (1 mole % based on the amount of the acetylene dicarboxylic acid) was added to the above solution and the reaction mixture was heated to 87° C. and held there for eight hours.

Partial precipitation of the product occurred during the Diels-Alder reaction. The reaction mixture was chilled (0°–5° C.) and about 120 milliliters of hexane to was added to the mixture which resulted in the precipitation of the remaining cycloaddition product.

The Diels-Alder adduct product (identified as Structure I; R=methyl), was recovered as a fine white powder (50.5 grams;, 91% yield) having a melting point range of 137°–141.5° C.

The carboxylic acid content (as determined by KOH/pyridine titration) was two equivalents/mole. Elemental analysis (calculated) for the white powder product was C:69.04%, H:7.96% and O:22.99%. Elemental analysis (found) was C:69.11%, H:7.98% and O:22.91%.

EXAMPLE 2

This example demonstrates the preparation of the compound represented by Structure II.

About 25 grams (0.089 mole) of the Structure I, Diels-Alder adduct product prepared according to the procedure of Example 1, were dissolved in a two phase mixture of chlorobenzene (50 grams) and water (50 grams, pH=7.4).

Sodium periodate (10 grams), potassium permanganate (0.45 gram) and tetrahexyl ammonium iodide (1.0 gram) were added and dissolved in the aqueous phase.

Next, a Lemieux-Von Rudloff oxidation was carried out at 25° C. for 22 hours and the residual oxidizing agent was destroyed with the addition of 2.5 grams of sodium hydrogen sulfite.

The organic layer (off yellow color) was separated and dried over 3.0 grams of magnesium sulfate. The drying agent was filtered and the chlorobenzene solvent was removed under vacuum (0.5 mm/40° C.).

The product which remained (Structure II; R=methyl) was a pale yellow oil (30.6 grams, 100% yield). The elemental analysis, the $^1$H NMR and the $^{13}$C NMR data obtained for the Structure II product are summarized below in Table I.

TABLE I

Elemental and NMR Data for the Compound of Structure II

Elemental Analysis:

|  | carbon | hydrogen | oxygen |
|---|---|---|---|
| Calculated (%) | 56.14 | 6.47 | 37.37 |
| Found (%) | 56.58 | 6.52 | 36.91 |

$^1$H NMR (δ, CDCl$_3$):

2.15, single-broad, 12H (—C(=O)—CH$_3$)

2.64, broadened singlet, 8H (—C—CH$_2$—)
10.8, broad singlet, 2H (D$_2$O exchangeable)

$^{13}$C NMR (decoupled, ppm, CDCl$_3$):

27.5 (—C—CO$_2$H)

29.5 (CH$_3$—C(=O)—)

40.5 (—C(=O)—CH$_2$—)

179 (—CO$_2$H)

208 (—C(=O)—)

EXAMPLE 3

This example demonstrates the preparation of the compounds represented by Structures III and IV.

About (30.6 grams) (0.089 mole) of the oxidized Diels-Alder adduct product (Structure II) prepared according to the procedure of Example 2, were dissolved in aqueous tetrahydrofuran (40% water) and neutralized with two equivalents of 50° C. triethylamine (18 grams, 0.178 mole).

The resulting solution was added to a 500 milliliter aqueous solution of sodium cyanide (17.5 grams, 0.357 mole) and hydrazine sulfate (23.14 grams, 0.178 mole).

The resulting solution was stirred for 3 hours at 45° C., then cooled to room temperature. The reaction solution was then acidified (to litmus) with 1% aqueous hydrochloric acid solution.

A sample aliquot was taken and extracted with diethylether. The ethereal layer was dried over magnesium sulfate, filtered and the diethylether was removed under vacuum.

An off white powder product was isolated (m.p. 101° C.), analyzed and identified as having the general formula of Structure III (R=methyl). Elemental analysis data of the product are summarized below.

|  | carbon | hydrogen | nitrogen | oxygen |
|---|---|---|---|---|
| Calculated (%) | 54.28 | 5.92 | 25.32 | 14.46 |
| Found (%) | 54.97 | 6.00 | 25.12 | 14.79 |

The remaining acidified reaction solvent was cooled to 5° C. in an ice bath and treated, dropwise, with a bromine/carbon tetrachloride solution (18% Br$_2$, 10 g) over 20 minutes. Excess bromine was destroyed with 5 grams of sodium hydrogen sulfite.

A white solid was isolated after extraction with diethyl ether, drying with magnesium sulfate and removal of the ethereal solvent.

The solid product was washed extensively (5×200 ml) with cold (5° C.) water, then dried in a vacuum desicator over calcium sulfate.

The white solid was recovered (28.6 grams, 73% yield) and was found to have a melting point of 132° C. (decomposition). Structure assignment (Structure IV; R=methyl) was made based on the $^1$H NMR, $^{13}$C NMR and $^{15}$N NMR data set forth in following Table II.

TABLE II

NMR Data for the Compound of Structure IV $^1$H NMR (δ, CDCl$_3$):

| 1.45, singlet, 12H | ($-CH_3$) |
|---|---|
| 1.8, doublet, 4H, J = 4Hz | Geminal |
| 1.9, doublet, 4H, J = 4Hz | $CH_2-$ |
| 11.2, singlet, 2H, D$_2$O exchangeable | |

$^{13}$C NMR (decoupled, ppm, CDCl$_3$):

12.5 (N≡C−$\underline{C}$(CH$_3$))

27.5 ($-\underline{C}-CO_2H$)

28.5 ($\underline{CH_2}-$)

53.6 ($-\underline{C}(CH_3)-C≡N$)

122 ($-\underline{C}≡N$)

181 ($-\underline{C}O_2H$)

$^{15}$N NMR (ppm, CH$_3$NO$_2$ relative):

−122.21 ($-C≡N$)

136.58 ($-N=N-$)

EXAMPLE 4

This example demonstrates the preparation of the initiator used in the practice of this invention which is represented by Structure V.

About 28.6 grams (0.065 mole) of the bicyclic azo compound of a Structure IV, prepared using the procedure of Example 3 were dissolved in a 200 ml mixture of tetrahydrofuran:water (2:1 vol/vol).

The resulting solution was cooled to 0° C. in a ice-/sodium chloride/water bath and triethylamine (13.1 grams, 0.180 mole) in 50 milliliters of tetrahydrofuran was added to the solution.

The reaction mixture was cooled to −20° C. with a dry ice/acetone slurry and a solution of ethyl chloroformate (3.51 grams, 0.032 mole) in 50 milliliters of tetrahydrofuran was added to the reaction mixture over 20 minutes.

The reaction mixture was stirred at −20° C. for one hour and a solution of sodium azide (2.2 grams, 0.032 mole) in 100 milliliters of water was added over a one hour period.

The reaction mixture allowed to warm to −5° C. and stirred again for one hour.

The reaction mixture was diluted with 1.5 volumes of water resulting in the precipitation of a pale yellow powder. The powder was purified by dissolving it in chloroform and precipitating with excess petroleum ether.

The pale yellow powder (20.3 grams, 70% yield) was found to have a melting point of 77° C. (decomposition).

On the basis of the following spectral data set forth in Table III, Structure V and the name [2, 5, 8, 11]-tetramethyl-[2, 5, 8, 11]-tetracyano-cis-6a'carboxy, 12a' oxoazide-3,4:9,10 bis diazobicyclooctane was assigned to the product:

TABLE III

Infrared and NMR Data for the Compound of Structure V

Infrared (CM$^{-1}$, CHCl$_3$):

1687 ($-\overset{O}{\overset{\|}{C}}-N_3$)

$^1$H NMR (δ, CDCl$_3$):

1.45, singlet 12H
1.8, doublet × doublet, 4H J = 4.5Hz
1.88, doublet × doublet, J = 4.5Hz
11.0, singlet, 1H, D$_2$O exchangeable $^{13}$C NMR (decoupled, ppm, CDCl$_3$)

12.5 (N≡C−$\underline{C}$(CH$_3$))

28.8 ($-\underline{C}-CO_2H$)

30.1 ($-\underline{C}-CON_3$)

28.1, 29.5 ($-\underline{CH_2}-$)

53.7 ($-\underline{C}(CH_3)-C≡N$)

122.2 ($-\underline{C}≡N$)

162.3 ($-\underline{C}(=O)-N_3$)

180.2 ($-\underline{C}(=O)-OH$)

$^{15}$N NMR (ppm, CH$_3$NO$_2$ relative)

a −233
b −138          $-\overset{O}{\overset{\|}{C}}-\underset{a}{N}=\underset{b}{N}=\underset{c}{N}$
c −133

−122.2 ($-C≡N$)

136.7 ($-N=N-$)

EXAMPLE 5

This example serves to demonstrate the preparation of a five arm radial block polymer of this invention having four arms of poly(n-butylacrylate-co-ethylacrylate) and a fifth arm of styrene/N-phenylmaleimide copolymer.

A hydroxyl terminated styrene/N-phenylmaleimide (S/N-PMI) copolymer was prepared by dissolving bis-2-hydroxylethyldisulfide (1.0 gram) and 2-hydroxy ethanethiol (0.8 gram) in a monomer solution consisting of 126 grams of N-phenylmaleimide, 74 grams of inhibitor free styrene and 40 grams of monochlorobenzene. The reaction mixture was heated to 85° C. for 10 hours. The resulting polymer mass was dissolved in tetrahydrofuran and recovered by precipitation in methanol. The molecular weight of the hydroxyl terminated S/N-PMI copolymer was determined by gas permeatation chromatography "GPC" (vs a polystyrene standard): Mw=34,400; Mn=12,600, peak molecular weight = 30,800. The copolymer contained 5.2 weight percent nitrogen which corresponds to 63 weight percent N-phenylmaleimide. The copolymer exhibited a glass transition temperature ("Tg") of 217.5° C. The hydroxyl functionality was determined by two methods (1) titration and (2) derivatization.

(1) Hydroxyl Content Via Titration 12.18 grams of hydroxyl functionalized S/N-PMI copolymer were dissolved in 100 grams of pyridine at 25° C. Acetic anhydride (1.2 grams) was added to the pyridine solution and warmed to 50° C. for 2.4 hours. Water (3.0 ml) was added and the reaction was maintained at 50° C. for 6.0 hours. A 1% phenolphthalein/pyridine solution (10 drops) was added to the pyridine solution once it had been cooled to 25° C. The solution was titrated with 0.103 N aqueous potassium hydroxide. The hydroxyl functionality was determined to be $2.11 \times 10^{-3}$ equivalents/gram of polymer.

(2) Derivatization with Isocyanatoethyl Methacrylate

Hydroxyl terminated S/N-PMI copolymer (25 grams) and isocyanatoethyl methacrylate (8.1 grams, 0.052 mole) were dissolved in 100 milliliters of ethylacetate containing 0.5 gram of dibutyl tin dilaurate. The reaction was warmed to 65° C. for 4 hours. The S/N-PMI copolymer was recovered by precipitation into methanol. The methylacrylate functionalization, hence hydroxyl functionalization of the S/N-PMI copolymer was assessed by copolymerization of the methacrylate terminated S/N-PMI macromonomer with n-butyl acrylate. Methacrylate terminated S/N-PMI copolymer (20 grams) and n-butylacrylate (80 grams) were combined in ethyl acetate (400 grams). An initiator, azobisisobutyronitrile (AIBN) (0.05 gram) was added to the monomer solution and the reaction heated to 60° C. for 17 hours. The polymer formed was recovered by precipitation into methanol followed by drying in a vacuum oven. The copolymer (yield = 86%) was completely soluble in tetrahydrofuran indicating little if any difunctional styrene/N-phenylmaleimide copolymer. Analysis of functionalization was accomplished by GPC. The copolymer sample exhibited a peak molecular weight of 197,600 (comprising 97% of trace) and a peak molecular weight signal of 30,800 (comprising 3% of trace). Therefore, based on the unreacted portion of functionalized S/N-PMI; the hydroxyl functionality of the S/N-PMI had a minimum value of 90%.

Approximately 50 grams of the resulting hydroxyl terminated S/N-PMI copolymer (Mn = 12,600) and 43.7 grams (0.097 mole) of the [2, 5, 8, 11] tetramethyl [2, 5, 8, 11]-tetracyano-cis-6a' carboxy, 12a' oxoazide-3,4:9,10 bisdiazobicyclooctane produced using the procedure of Example 4 were dissolved in 150 grams of dry chlorobenzene. The reaction mixture was heated to 60° C. for 12 hours. The chlorobenzene polymer solution was poured into excess methanol. The S/N-PMI copolymer recovered exhibited a Mn of 13,100 and a Tg by Differential Scanning Calorimetry "DSC" of 216.5° C. An aliquot of the chlorobenzene reaction mixture was analyzed by liquid chromatography against control samples of the hydroxyl functionalized S/N-PMI copolymer and the diazo initiator. The unreacted diazo initiator was determined to be 7.3% by weight. This correlates well with the calculated functionality of the S/N-PMI copolymer. Thus, it was confirmed that the hydroxyl group of the S/N-PMI copolymer reacted through the -carboxy carbonylazide functionality.

The bisdiazobicyclooctane functionalized S/N-PMI copolymer (58.5 grams) (including the 7.3% by weight unreacted diazo initiator) was dissolved in an ethyl acetate/n-butylacrylate/ethyl acrylate solution (600/165/25 grams). The reaction was heated to 85° C. for 72 hours. The polymer formed was recovered by devolatilization in a vacuum oven at 30 mm Hg/50° C./5 days. The total radial block polymer recovered was 264 grams (79.5% conversion of comonomer mixture to polymer). The radial block polymer exhibited two glass transition temperatures 217° C. (S/N-PMI) and −27.5° C. (n-butylacrylate/ethyl acrylate copolymer). GPC analysis of the radial block polymer revealed an Mn of 292,700. Based on the GPC analysis there was no unreacted (free) functionalized S/N-PMI copolymer. However, the molecular weight characteristics of the polymer did exhibit some bimodal character as evidenced by the second, but minor Mn of 131,750. The ratio of the area under the GPC traces for the high Mn:low Mn was 88:12. The gel content of the radial block polymer was approximately 8 to 10%.

EXAMPLE 6

This example serves to demonstrate the preparation of a five arm radial block polymer of this invention having four arms of poly (n-butylacrylate-co-ethylacrylate) and a fifth arm of poly(methylmethacrylate).

A hydroxyl terminated poly(methyl methacrylate) (PMMA) was prepared by dissolving bis-2-hydroxylethyldisulfide (1.0 gram) and 2-hydroxy ethanethiol (0.5 gram) in 200 grams of inhibitor free methyl methacrylate monomer. The reaction mixture was heated to 85° C. for 24 hours. The polymer mass was dissolved in tetrahydrofuran and recovered by precipitation into methanol. The molecular weight of the hydroxyl terminated PMMA was determined by GPC (vs a polystyrene standard): MW = 49,970; Mn = 26,300; peak molecular weight = 39,880. The conversion of methyl methacrylate monomer to polymer was 87%. The hydroxyl functionality was determined by two methods: (1) titration and (2) derivatization.

(1) Hydroxyl Content Via Titration 10.12 grams of hydroxylfunctionalized PMMA were dissolved in 100 grams of pyridine at 25° C. Acetic anhydride (1.0 gram) was added to the pyridine solution and warmed to 50° C. for 2.0 hours. Then 3.0 milliliters of water were added and the reaction was maintained at 50° C. for 6.0 hours. A 1% phenolphthalein/pyridine solution (10 drops) was added to the pyridine solution once it had been cooled to 25° C. The solution was titrated with 0.010 N aqueous potassium hydroxide. The hydroxyl functionality was determined to be $1.9 \times 10^{-3}$ equivalents/gram of polymer.

(2) Derivatization with Isocyanatoethyl Methacrylate

Hydroxyl terminated PMMA (25 grams) and isocyanatoethyl methacrylate (7.5 grams, 0.048 mole) were dissolved in 100 milliliters of ethyl acetate containing 0.5 grams of dibutyl tin dilaurate. The reaction was warmed to 65° C. for 4 hours. The PMMA polymer was recovered by precipitation into methanol. The methylacrylate functionalization, hence hydroxyl functionalization of the PMMA polymer was assessed by copolymerizing the methacrylate terminated PMMA macromonomer with n-butyl acrylate.

Methylacrylate terminated PMMA (20 grams) and n-butyl acrylate (80 grams) were combined in ethyl acetate (400 grams). An initiator, AIBN (0.05 gram) was added to the monomer solution and the reaction heated to 60° C. for 17 hours. The polymer formed was recovered by precipitation into methanol followed by drying in a vacuum oven. The copolymer (88%) was completely soluble in tetrahydrofuran indicating little if any difunctional (hydroxyl) PMMA. Analysis of functionalization was ascertained via GPC. The copolymer sample exhibited a peak molecular weight of 202,700 (comprising 98% of trace) and a small peak molecular weight signal of 27,350 (comprising 2% of trace). Therefore, based on the unreacted portion of functionalized PMMA; the (hydroxyl) functionality of the PMMA had a minimum value of 90%.

Approximately, 50 grams of hydroxyl terminated PMMA (Mn=26,3000) and 43.46 grams (0.095 mole) of [2, 5, 8, 11]-tetramethyl-[2, 5, 8, 11]-tetracyano-cis-6a' carboxy, 11a' oxoazide 3,4:9,10 -bisdiazobicyclooctane were dissolved in 150 grams of dry chlorobenzene. The reaction mixture was heated to 60° C. for 12 hours. The chlorobenzene polymer solution was poured into excess methanol. The PMMA polymer recovered exhibited a Mn of 27,800 and a Tg (°C., DSC) of 72. An aliquot of the chlorobenzene reaction mixture was analyzed by liquid chromatography against control samples of the hydroxyl functionalized PMMA and the diazo initiator. The unreacted diazo initiator was determined to be 8.2% by weight. This correlates well with the calculated functionality of the PMMA. Thus, it was confirmed that the hydroxyl group of the PMMA reacted through the carboxy carbonyl azide functionality.

The bisdiazobicyclooctane functionalized poly(methylmethacrylate) (160 grams) was dissolved in an ethyl acetate/n-butylacrylate/ethylacrylate solution (600/165/75 grams). The reaction was heated to 85° C. for 72 hours. The polymer formed was recovered by devolatilization in a vacuum oven at 30 mmHg/50° C./5 days. The total radial block polymer recovered was 271 grams (81% conversion of comonomer mixture to polymer). The radial block polymer exhibited two glass transition temperatures 73° C. (PMMA) and −29° C. (n-butylacrylate/ethylacrylate copolymer). GPC analysis of the radial block polymer revealed an Mn of 289,400. Based on the GPC analysis there was no unreacted (free) functionalized PMMA. However, the molecular weight characteristics of the radial block polymer did exhibit some bimodal character as evidenced by a second, but minor Mn of 127,600. The ratio of the area under the GPC traces for the high Mn:low Mn was 86:14. The gel content of the radial block polymer as determined by centrifigation of the sample was approximately 6 to 8%.

EXAMPLE 7

This example demonstrates the preparation of a four arm radial block polymer of this invention having four poly(n-butylacrylate-co-ethylacrylate) arms.

About 1 gram of [2,5,8,11]-tetramethyl-[2,5,8,11]-tetracyano-cis-6a' carboxy, 11a'-oxoazide 3,4,:9,10-bis-diazobicyclooctane is dissolved in an ethyl acetate/n-butylacrylate/ethylacrylate solution · (600/165/75 grams). The reaction is heated to 85° C. for 72 hours. The polymer formed is recovered by devolatilization in a vacuum oven at 300 mmHg/50° C./5 days. The radial block copolymer is recovered and has four arms of poly(b-butylacrylate-co-ethylacrylate) and exhibits a Tg of −29° C.

EXAMPLE 8

This example serves to demonstrate the preparation of molded composition of this invention which employs the radial block polymer prepared in Example 6 consisting of one PMMA arm and four poly(n-butylacrylate-co-ethylacrylate) arms as an impact modifier for styrene/maleic anhydride copolymers.

A physical mixture comprising 800 grams of Dylark ® 332 styrene/maleic anhydride copolymer (ARCO Chemical Company); 200 grams of the radial block polymer prepared in Example 6; 2.0 grams of Ultranox ® 256 antioxidant (polymeric, sterically hindered phenol, Borg-Warner Chemicals, Inc.); and 1.5 grams of Ultranox ® 626 antioxidant (Bis(2,4-di-t-butylphenyl) pentaerythritol diphosphite) was prepared. The mixture was extruded, pelletized and test specimens were injection molded for physical property analysis (Table IV).

TABLE IV

| | | |
|---|---|---|
| (DYLARK ® 332 resin (14% MA) | 100 | 80 |
| Radial block polymer (Ex. 6) | 0 | 20 |
| Tg (°C., DSC) | 130.5 | 128.5 |
| Tensile str (psi) | 7,300 ± 82 | 6,900 ± 68 |
| Flex str (psi) | 11,800 ± 212 | 10,100 ± 123 |
| Flex mod (psi) | 461,700 ± 12,840 | 337,000 ± 11,084 |
| DTUL (°F., ⅛″) | 214 | 210 |
| Notched Izod (ft.-lbs/in.) | 0.5 | 4.2 ± 0.1 |
| GFWI (in.-lbs.) | <2 | 176 |
| Elongation (%) | 1.9 ± 0.5 | 23 ± 3 |

EXAMPLE 9

This example serves to demonstrate the preparation of a molded composition of this invention which employs the radial polymer prepared in Example 6 consisting of one PMMA arm and four poly(n-butylacrylate-co-ethylacrylate) arms as an impact modifier for polycarbonate.

A physical mixture comprising 1000 grams of Merlon ® M-50 polycarbonate resin (Mobay Corp.) and 50 grams (5 phr) of the radial block polymer prepared in Example 6 stabilized with 2.0 grams of Ultranox ® 256 antioxidant was prepared. The mixture was extruded, pelletized and test specimens were injection molded for physical property analysis (Table V).

TABLE V

| | | |
|---|---|---|
| Merlon ® Polycarbonate (M-50) | 100 | 100 |
| Radial Block polymer (Example 6) | 0 | 5 phr |
| Tensile str (psi) | 8,400 | 8,327 |
| Flex mod (psi) | 350,900 | 345,940 |
| DTUL (⅛″, °F.) | 256 | 256 |
| Notched Izod (ft.-lbs./in.) | | |
| ⅛″ unannealed | 17.2 | 18.6 |
| ¼″ unannealed | 5.4 | 15.1 |
| ⅛″ annealed | 3.2 | 12.2 |
| ¼″ annealed | 3.0 | 10.1 |
| Elongation (%) | 52 | 56 |

EXAMPLE 10

This example serves to demonstrate the preparation of a molded composition of this invention which employs the radial block polymer of Example 5 consisting of one S/N-PMI arm and four poly(n-butylacrylate-co-ethylacrylate) arms as an impact for styrene/acrylonitrile copolymer.

A physical mixture comprising 750 grams of Lustran®-31, a styrene/acrylonitrile copolymer (23.2 wt % acrylonitrile) available from Monsanto Company; 250 grams of the radial polymer produced in Example 5; 1.5 grams of Ultranox 626 antioxidant, 1.5 grams of Weston TNPP (trinonylphenylphosphite) and 2.0 grams of Ultranox 256 antioxidant was prepared. The mixture was extruded, pelletized and test specimens were injection molded for physical property analysis. (Table VI).

TABLE VI

| | | |
|---|---|---|
| Lustran ®-31 SAN resin | 100 | 75 |
| Radial Block polymer (Ex. 5) | 0 | 25 |
| Tg (°C., DSC) | 109 | 113 |
| Tensile str (psi) | 9,300 | 5,918 |
| Flexural modulus (psi) | 410,000 | 327,400 |
| DTUL (⅛", °F.) | 181 | 175 |
| Notched Izod (ft-lbs/in) | 0.7 | 9.2 |
| GFWI (in-lbs) | 0 | 280 |
| Elongation (%) | 2.1 | 38 |

EXAMPLE 11

This example serves to demonstrate the preparation of a molded composition of this invention which employs the radial block polymer of Example 5 consisting of one S/N-PMI arm and four poly(n-butylacrylate-co-ethylacrylate) arms as an impact modifier for S/N-PMI copolymer.

A physical mixture comprising 750 grams of styrene/N-phenylmaleimide copolymer (37/63 wt %); 250 grams of the radial block polymer of Example 5, 1.5 grams of Ultranox 626 antioxidant; 1.5 grams of Weston TNPP; and 2.0 grams of Ultranox 256 antioxidant was prepared. The mixture was extruded, pelletized and test specimens were injection molded for physical property analysis. (Table VII).

TABLE VII

| | | |
|---|---|---|
| S/N-PMI (37/63 wt %) | 100 | 75 |
| Radial block polymer (Ex. 5) | 0 | 25 |
| Tg (°C. DSC) | 220 | 219 |
| Tensile str (psi) | 6,840 | 5,760 |
| Flexural Modulus (psi) | 596,700 | 400,800 |
| DTUL (⅛", °F.) | 375 | 300 |
| Notched Izod (ft-lbs/in) | 0.5 | 2.3 |
| GFWI (in-lbs) | 0 | 88 |
| Elongation (%) | 1.1 | 12 |

The data of Tables IV-VII show that the radial block polymers of this invention are suitable for use to impact modify and suitable thermoformable plastic resin.

The radial block polymer of this invention can be blended with any thermoformable plastic resins in amounts within the broad ranges—typically, from about 1 to about 99 weight percent thermoformable plastic resin to about 99 to about 1 weight percent radial block polymer.

Moreover, the five arm radial block polymers of this invention, having 5 arms wherein each $(A)_n$ arm is comprised of recurring units of monomer(s) having a $Tg \leq 0°$ C. and the $(B)_n$ arm is comprised of recurring units of monomer(s) having a $Tg \geq 25°$ C., are particularly well suited to impart excellent impact resistance to thermoformable plastic resins when incorporated therein into. Thermoformable plastic resins which can be impact modified include styrene/maleic anhydride co- and terpolymers, styrene/acrylonitrile co- and terpolymers, (e.g. styrene/acrylonitrile/N-PMI) styrene/methacrylic acid co- and terpolymers, styrene/methylmethacrylate co- and terpolymers, styrene/maleimide co- and terpolymers, styrene/N-substituted maleimide co- and terpolymers, (e.g. styrene/maleic anhydride/N-PMI) polycarbonate blends, polybutylene terephthalate, PBT blends, polyamides, polyamide blends, polyarylate resins, polysulfone resins and the like and their mixtures.

The amount of five arm radial block polymer which is incorporated into the thermoformable plastic resin is an effective amount to improve the impact resistance of the thermoformable plastic resin upon molding. Typically, the amount of radial block polymer incorporated in weight percent, will be within the range of from about 1 to about 50, preferably from about 5 to about 30.

The molded compounds of this invention can also include other ingredients such as extenders, processing aids, pigments, mold release agents and the like, for their conventionally employed purposes. Also, reinforcing fillers in amounts sufficient to impart reinforcement can be used, such as titanium dioxide, potassium titanate and titanate whiskers, glass flakes and chopped glass fibers.

It will be evident from the foregoing that various modifications can be made to this invention. Such, however, are considered as being within the scope of the invention.

What is claimed is:

1. A radial block polymer having at least four arms and the following general formula:

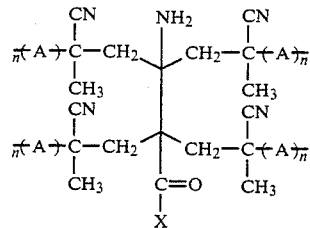

wherein each R separately represents a methyl or ethyl moiety; each A separately represents at least one free radically polymerizable monomer; X represents —OH, —O(B)$_n$, —S—(B)$_n$ or NH(B)$_n$; B represents at least one free radically polymerizable monomer; and, each n separately represents an integer greater than or equal to 50.

2. The polymer of claim 1 in which each $(A)_n$ represents poly(n-butylacrylate-co-ethylacrylate).

3. The polymer of claim 1 in which $(B)_n$ represents styrene/N-phenylmaleimide copolymer.

4. The polymer of claim 1 in which $(B)_n$ represents polymethylmethacrylate.

5. A moldable composition comprising a thermoformable plastic resin and a radial block polymer having the following general formula:

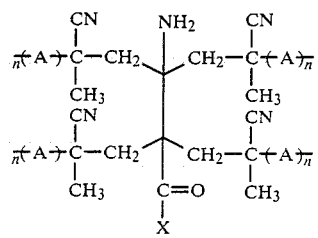

wherein each R separately represents a methyl or ethyl moiety; each A separately represents at least one free radically polymerizable monomer; X represents —OH, —O(B)$_n$, —S(B)$_n$, or NH(B)$_n$; B represents at least one free radically polymerizable monomer; and, each n separately represents an integer greater than or equal to 50.

6. The composition of claim 5 containing a reinforcing filler.

7. A method of producing a molded composition which comprises forming a blend comprising a thermoformable plastic resin and a radial block polymer having the following general formula:

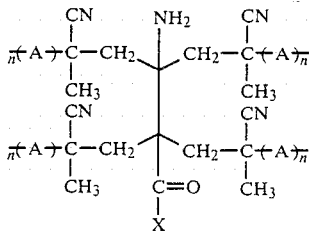

wherein each R separately represents a methyl or ethyl moiety; each A separately represents at least one free radically polymerizable monomer; X represents —OH, —O(B)$_n$, —S(B)$_n$ or —NH(B)$_n$; B represents at least one free radically polymerizable monomer; and, each n separately represents an integer greater than or equal to 50, and molding the resulting blend.

8. The method of claim 7 in which said blend is molded in contact with a reinforcing filler.

9. A molded composition comprising a continuous phase comprising a thermoformable plastic resin and a disperse phase within the continuous phase, the disperse phase being a radial block polymer having the following general formula:

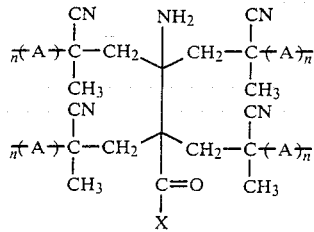

wherein each R separately represents a methyl or ethyl moiety; each A separately represents at least one free radically polymerizable monomer; X represents —OH, —O(B)$_n$, —S(B)$_n$, or —NH(B)$_n$; B represents at least one a free radically polymerizable monomer; and, each n separately represents an integer greater than or equal to 50.

10. A method of improving the impact resistance of a thermoformable plastic resin upon molding which comprises incorporating into a continuous phase thermoformable plastic resin, a disperse phase comprising a five arm radial block polymer having the following general formula:

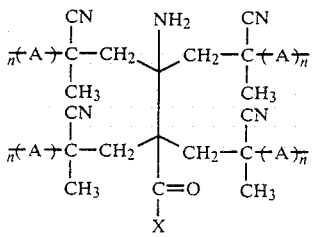

wherein each R separately represents a methyl or ethyl moiety; each A separately represents at least one free radically polymerizable monomer having a glass transition temperature $\leq 0°$ C; X represents —O(B)$_n$, —S(B)$_n$ or —NH(B)$_n$; B represents at least one free radically polymerizable monomer having a glass transition temperature $\geq 25°$ C; and, each n separately represents an integer greater than or equal to 50, the radial block polymer being incorporated in an amount sufficient to improve the impact resistance of the thermoformable plastic resin upon molding.

* * * * *